United States Patent
Zhang et al.

(10) Patent No.: US 11,408,816 B2
(45) Date of Patent: Aug. 9, 2022

(54) DEVICE AND METHOD FOR DRY-WET CYCLE SIMULATION TEST OF CONCRETE IN TIDAL ZONE AND SPLASH ZONE

(71) Applicant: QINGDAO UNIVERSITY OF TECHNOLOGY, Qingdao (CN)

(72) Inventors: Peng Zhang, Qingdao (CN); Jiuwen Bao, Qingdao (CN); Jianan Wei, Qingdao (CN); Zhijie Zhuang, Qingdao (CN); Tiejun Zhao, Qingdao (CN)

(73) Assignee: QINGDAO UNIVERSITY OF TECHNOLOGY, Qingdao (CN)

( * ) Notice: Subject to any disclaimer, the term of this patent is extended or adjusted under 35 U.S.C. 154(b) by 66 days.

(21) Appl. No.: 17/058,564

(22) PCT Filed: Feb. 14, 2020

(86) PCT No.: PCT/CN2020/075301
§ 371 (c)(1),
(2) Date: Nov. 24, 2020

(87) PCT Pub. No.: WO2020/192294
PCT Pub. Date: Oct. 1, 2020

(65) Prior Publication Data
US 2021/0190672 A1     Jun. 24, 2021

(30) Foreign Application Priority Data
Mar. 28, 2019    (CN) .......................... 201910242425.6

(51) Int. Cl.
*G01N 17/00*     (2006.01)
*G01N 33/38*     (2006.01)

(52) U.S. Cl.
CPC ......... *G01N 17/002* (2013.01); *G01N 33/383* (2013.01); *G01N 2203/0242* (2013.01)

(58) Field of Classification Search
CPC ............................ G01N 17/02; G01N 17/002
(Continued)

(56) References Cited

U.S. PATENT DOCUMENTS 3,327,536 A * 6/1967 Fitzgerald .............. G01N 17/00
55/385.2
4,012,954 A * 3/1977 Klippert ............... G01N 17/004
73/159
(Continued)

FOREIGN PATENT DOCUMENTS

| CN | 201844965 U | 5/2011 |
| CN | 103091236 A | 5/2013 |

(Continued)

OTHER PUBLICATIONS

Mehdi Khanzadeh-Moradllo et al., "Effect of Wet Curing Duration on Long-Term Performance of Concrete in Tidal Zone of Marine Environment", International Journal of Concrete Structures and Materials, vol. 9, No. 4, pp. 487-498, Dec. 2015. (Year: 2015).*

(Continued)

*Primary Examiner* — David A. Rogers
(74) *Attorney, Agent, or Firm* — Armstrong Teasdale LLP

(57) ABSTRACT

The disclosure relates to a device and method for a dry-wet cycle simulation test of concrete in a tidal zone and a splash zone. A main structure includes a liquid storage tank, a test chamber, a communicating pipe, air holes of the liquid storage tank, air holes of the test chamber, ceiling fans, steel pipes, a support frame, an upper water level sensor, a lower water level sensor, a temperature and humidity sensor, a temperature sensor, a chamber body support, a communication valve, a pipe support, a water inlet pump, a water inlet valve, a water outlet pipe, a water outlet pump, a water outlet valve, spray water pipes, spray heads, and a control box. The control box can control and record test parameters in real (Continued)

time, so that the boundary between the tidal zone and the splash zone is clear.

12 Claims, 2 Drawing Sheets

(58) Field of Classification Search
USPC .................................................. 73/865.8
See application file for complete search history.

(56) References Cited

U.S. PATENT DOCUMENTS

| | | | | |
|---|---|---|---|---|
| 4,282,181 | A * | 8/1981 | Pierce | G01N 17/00 |
| | | | | 422/53 |
| 4,807,247 | A * | 2/1989 | Robbins, III | G01N 17/004 |
| | | | | 374/57 |
| 5,187,987 | A * | 2/1993 | Anderson | G01N 3/20 |
| | | | | 73/865.6 |
| 5,285,672 | A * | 2/1994 | Yao | G01N 33/0047 |
| | | | | 73/865.6 |
| 5,851,143 | A * | 12/1998 | Hamid | G01R 31/2849 |
| 6,272,767 | B1 * | 8/2001 | Botruff | B01L 1/00 |
| | | | | 34/210 |
| 6,799,471 | B1 * | 10/2004 | Regimand | G01N 33/42 |
| | | | | 73/803 |
| 6,990,847 | B2 * | 1/2006 | Happach | G01N 25/66 |
| | | | | 374/E70.18 |
| 7,380,466 | B2 * | 6/2008 | Deeg | G01N 33/383 |
| | | | | 73/803 |
| 7,647,821 | B2 * | 1/2010 | Bloomquist | G01N 3/24 |
| | | | | 73/865.6 |
| 7,784,367 | B2 * | 8/2010 | Kojima | C09D 11/32 |
| | | | | 347/100 |
| 10,285,304 | B1 * | 5/2019 | Lin | H05K 7/20745 |
| 2004/0231440 | A1 * | 11/2004 | Beraud | G01N 17/004 |
| | | | | 73/865.6 |
| 2021/0389230 | A1 * | 12/2021 | Deurloo | G01N 17/002 |

FOREIGN PATENT DOCUMENTS

| | | | | |
|---|---|---|---|---|
| CN | 203643310 | U | | 6/2014 |
| CN | 104849201 | A | | 8/2015 |
| CN | 103217353 | B * | 10/2015 | ............. G01N 17/02 |
| CN | 105445173 | A | | 3/2016 |
| CN | 105547977 | A * | 5/2016 | |
| CN | 105547978 | A * | 5/2016 | |
| CN | 105954178 | A * | 9/2016 | |
| CN | 205691470 | U | | 11/2016 |
| CN | 106918545 | A * | 7/2017 | |
| CN | 107036958 | A * | 8/2017 | |
| CN | 107389541 | A * | 11/2017 | |
| CN | 107491595 | A | | 12/2017 |
| CN | 107741370 | A * | 2/2018 | |
| CN | 107741395 | A * | 2/2018 | ............. G01N 17/00 |
| CN | 104568723 | B * | 3/2018 | |
| CN | 207114545 | U * | 3/2018 | |
| CN | 107894392 | A * | 4/2018 | ............. G01B 7/02 |
| CN | 207366416 | U * | 5/2018 | |
| CN | 108226020 | A * | 6/2018 | ............. G01N 17/02 |
| CN | 207472737 | U * | 6/2018 | |
| CN | 105588751 | B * | 8/2018 | ............. G01N 17/02 |
| CN | 105675479 | B * | 8/2018 | ........... G01N 17/002 |
| CN | 108414432 | A * | 8/2018 | ............. G01N 17/00 |
| CN | 108693105 | A * | 10/2018 | |
| CN | 108760610 | A | | 11/2018 |
| CN | 208043828 | U * | 11/2018 | |
| CN | 208091880 | U | | 11/2018 |
| CN | 208109663 | U * | 11/2018 | |
| CN | 109269971 | A * | 1/2019 | ........... G01N 17/002 |
| CN | 109406378 | A * | 3/2019 | |
| CN | 109813878 | A | | 5/2019 |
| CN | 110196222 | A * | 9/2019 | |
| CN | 111707602 | A * | 9/2020 | |
| CN | 112525809 | A * | 3/2021 | |
| CN | 113237820 | A * | 8/2021 | |
| DE | 10155245 | B4 * | 12/2004 | .......... G01M 17/007 |
| DE | 102012221673 | A1 * | 5/2014 | .......... G01N 17/002 |
| DE | 102018105754 | A1 * | 9/2018 | ................ B01L 1/00 |
| FR | 3042865 | A1 * | 4/2017 | |
| JP | 63208760 | A | | 8/1988 |
| JP | 2007003250 | A | | 1/2007 |
| KR | 20040039892 | A * | 5/2004 | |
| KR | 20120090603 | A * | 8/2012 | |
| WO | WO-9747961 | A1 * | 12/1997 | ............. G01N 17/00 |

OTHER PUBLICATIONS

Dharam Paul, "Weathering of hardened concrete causes and suggested remedies", Indian Concrete Journal, Apr. 1983. (Year: 1983).*
S. K. Roy et al., "Durability of concrete accelerated carbonation and weathering studies", Building and Environment, vol. 34, 1999. (Year: 1999).*
Caijun Shi et al., "Weathering properties of CO2-cured concrete blocks", Resources, Conservation and Recycling, vol. 65, 2012. (Year: 2012).*
M.D.A. Thomas et al., "The Performance of Concrete in a Marine Environment", Sixth International Conference on Durability of Concrete Structures, Jul. 18-20, 2018. (Year: 2018).*
Géraldine Villain et al., "Durability diagnosis of a concrete structure in a tidal zone by combining NDT methods: Laboratory tests and case study", Construction and Building Materials, vol. 37, 2012. (Year: 2012).*
Chloe Yan Chan et al., "Assessment of Carbon Sequestration Potential of Concrete Blocks With an Accelerated Environmental Exposure Chamber", 13th Canadian Masonry Symposium, Jun. 4-7, 2017. (Year: 2017).*
ESPACENET Machine Translation of CN 103217353 B Which Originally Published on Oct. 14, 2015. (Year: 2015).*
ESPACENET Machine Translation of CN 105445173 A Which Originally Published on Mar. 30, 2016. (Year: 2016).*
ESPACENET Machine Translation of CN 105547977 A Which Originally Published on May 4, 2016. (Year: 2016).*
ESPACENET Machine Translation of CN 105547978 A Which Originally Published on May 4, 2016. (Year: 2016).*
ESPACENET Machine Translation of CN 107036958 A Which Originally Published on Aug. 11, 2017. (Year: 2017).*
ESPACENET Machine Translation of CN 107389541 A Which Originally Published on Nov. 24, 2017. (Year: 2017).*
ESPACENET Machine Translation of CN 107741395 A Which Originally Published on Feb. 27, 2018. (Year: 2018).*
ESPACENET Machine Translation of CN 110196222 A Which Originally Published on Sep. 3, 2019. (Year: 2019).*
ESPACENET Machine Translation of JP S 63208760 A Which Originally Published on Aug. 30, 1988. (Year: 1988).*
PCT International Search Report and Written Opinion, Application No. PCT/CN2020/075301, dated May 26, 2020, 12 pps.: with English Translation.

* cited by examiner

DEVICE AND METHOD FOR DRY-WET CYCLE SIMULATION TEST OF CONCRETE IN TIDAL ZONE AND SPLASH ZONE

CROSS REFERENCE TO RELATED APPLICATIONS

This patent application is a National Stage Entry of PCT/CN2020/075301 filed on Feb. 14, 2020, which claims the benefit and priority of Chinese Patent Application No. 201910242425.6 filed on Mar. 28, 2019, the disclosures of which are incorporated by reference herein in their entirety as part of the present application.

BACKGROUND

The disclosure belongs to the technical field of equipment for durability tests of marine concrete materials, and particularly relates to a device and method for a dry-wet cycle simulation test of concrete in a tidal zone and a splash zone.

Concrete structures in marine environments work in severe conditions since the concrete is under the action of complex factors such as dry-wet cycles, freeze-thaw cycles, ion erosion, and seawater corrosion. Accordingly, the durability problem caused by chloride ingress into concrete in marine environment is far more serious than that of concrete in general atmospheric environments. Dry-wet cycle is one of the most unfavorable impacts on the durability of concrete. For the marine concrete under the action of dry-wet cycle for a long time, the exchange of chloride ions between the external environment and the internal environment of concrete is accelerated, resulting in a significant increase in the chloride ion content and an inward diffusion rate in concrete. Dry-wet cycle occurs in a tidal zone and a splash zone due to the change of water level at rising tide and falling tide. In these zones, the erosion to concrete members caused by chloride ions is more serious than that in an underwater zone.

At present, there are many methods for simulating the accelerated test of dry-wet cycle of concrete, which can be roughly divided into two categories, one is to perform the simulation test by manual operation, and the other is to perform simulation test by an automatic device.

Chinese patent No. 201710612592.6 discloses a method for probability prediction of a concentration of chloride ions on a concrete surface in a marine splash zone. The method includes the following steps: (1) establishing a random sample point calculation model of a concentration of chloride ions on the concrete surface in the marine splash zone; establishing, according to a water-binder ratio and exposure time of the concrete, a random sample point calculation model of a concentration Cs of the chloride ions on the concrete surface in the marine splash zone:

$$C_{s,j} = \alpha_{1j}(\alpha_{2j} R_{W/B} + \alpha_{3j})(1 - e^{-\alpha_{4j}t}) + \alpha_{5j} + \xi \sigma$$

where $C_{s,j}$ is a j-th random sample point of the concentration $C_s$ of the chloride ions on the concrete surface in the marine splash zone, calculated by the percentage of their weight in the weight of a cementing material; $\alpha_{ij}$ ($i=1, 2, \ldots, 5$; $j=1, 2, \ldots, N$) is a j-th random sample point of an i-th probability model parameter; N is the number of random sample points; $R_{W/B}$ is the water-binder ratio; t is the exposure time calculated by year; $\xi$ is a standard normal distribution random variable; $\sigma$ is a standard deviation of a system error, calculated by the percentage in the weight of the cementing material; (2) determining statistical characteristic values of probability model parameters of different kinds of concrete in the marine splash zone, and generating random sample points of the probability model parameters: according to the type of concrete, determining a probability distribution type, a mean standard deviation and a correlation coefficient of a probability model parameter $\alpha_i$ ($i=1, 2, \ldots, 5$), and performing random sampling by a Monte Carlo method according to the probability distribution type, the mean standard deviation and the correlation coefficient of the probability model parameter $\alpha_i$ ($i=1, 2, \ldots, 5$), each probability model parameter $\alpha_i$ ($i=1, 2, \ldots, 5$) generating N random sample points $\alpha_{ij}$ ($i=1, 2, \ldots, 5$; $j=1, 2, \ldots, N$); (3) generating random sample points of the concentration of the chloride ions on the concrete surface in the marine splash zone to determine a probability density function of the concentration of the chloride ions on the concrete surface in the marine splash zone: sequentially substituting the N random sample points $\alpha_{ij}$ ($i=1, 2, \ldots, 5$; $j=1, 2, \ldots, N$) of the probability model parameter $\alpha_i$ ($i=1, 2, \ldots, 5$) generated in step (2) into the random sample point calculation model of the concentration of the chloride ions on the concrete surface in the marine splash zone in step (1), generating N random sample points $c_{s,j}$ ($j=1, 2, \ldots, N$) of the concentration $C_s$ of the chloride ions on the concrete surface in the marine splash zone, and calculating a mean and a standard deviation of the concentration $C_s$ of the chloride ions on the concrete surface in the marine splash zone according to a calculation model of the mean and the standard deviation of the concentration $C_s$ of the chloride ions on the concrete surface in the marine splash zone, thereby determining the probability density function of the concentration $C_s$ of the chloride ions on the concrete surface in the marine splash zone.

Chinese patent No. 201810522616.3 discloses a testing device for simulating corrosion of a reinforced concrete structure in a seawater splash environment, which includes a pool, where a middle portion of the pool is provided with a cushion block, the pool is filled with sodium chloride solution with a height greater than that of the cushion block, and the top of the cushion block is provided with a reinforced concrete member. A three-tenth portion of the periphery of a bottom end of the reinforced concrete member is provided with an epoxy resin coating, a side wall of a four-tenth portion of the reinforced concrete member at the top of the epoxy resin coating is provided with a PVC thermoplastic pipe, the top of the PVC thermoplastic pipe is fixedly installed at one end of a plastic hose, and the other end of the plastic hose is fixedly installed on a water outlet of a water pump. The water pump is located at the bottom of the pool. A steel bar at a top portion of the reinforced concrete member is connected to a positive pole of a direct current power supply through a wire, a negative pole of the direct current power supply is connected to a stainless steel sheet through a wire, and the stainless steel sheet is located in the pool and extends to the sodium chloride solution.

Chinese patent No. 201020579952.0 discloses a testing device for accelerated simulation of chloride erosion of concrete in a seawater tidal zone, which includes a test chamber A, water pump A, a water level sensor group A, a test chamber B, a water pump B, a water level sensor group B, and a power supply and control system, where the power supply and control system includes a water level controller A, a microcomputer time switch A, a water level controller B and a microcomputer time switch B; bottoms of both the test chamber A and the test chamber B are each provided with a conversion joint, the conversion joint arranged at the bottom of the test chamber A is connected to a water inlet end of the water pump A through a water pump inlet pipe, and a water outlet end of the water pump A extends into the test chamber B. The conversion joint arranged at the bottom of the test chamber B is connected to a water inlet end of the water pump B through a water pump inlet pipe, and a water outlet end of the water pump B extends into the test chamber A. The water level controller A is connected to the microcomputer time switch A, a control output end of the water level controller A is connected to the water pump A, an input end of the water level controller A is connected to the water level sensor group A, and the water level controller B is connected to the microcomputer time switch B. A control output end of the water level controller B is connected to the water pump B, and an input end of the water level controller B is connected to the water level sensor group B. The water level sensor group A is arranged in the test chamber A or the test chamber B, and the water level sensor group B is arranged in the test chamber A or the test chamber B.

Chinese patent No. 201510271667.X discloses a device for a durability impact test of coastal reinforced concrete under the action of alternation of wetting and drying, which includes a main water tank, an auxiliary water tank, water pumps, a porous barrier, a buoyancy tank, a clump weight and a water level control system, where the main water tank and the auxiliary water tank are each provided with a water inlet and a water outlet. The water inlets and the water outlets of the main water tank and the auxiliary water tank are arranged at the bottom of the water tank. The water inlet of the main water tank is connected to the water outlet of the auxiliary water tank through one water pump, and the water inlet of the auxiliary water tank is connected to the water outlet of the main water tank through one water pump. The porous barrier is arranged on a lower portion of the main water tank, and a concrete sample is placed on the porous barrier. The buoyancy tank is arranged on an upper portion of the main water tank, and the clump weight is arranged on the buoyancy tank. The water level control system includes a pressure sensor and a programmable logic controller (PLC), where the pressure sensor is arranged at the bottom of the main water tank and connected to the PLC, and a control end of each water pump is connected to the PLC.

However, it is found that the two kinds of methods each only singly simulate an environment in the dry-wet cycle test of concrete, without considering the synergistic effect of the tidal zone and the splash zone. This is inconsistent with the combined effect of tide and splash which concrete is subjected to when undergoing an exposed test in real sea.

BRIEF DESCRIPTION

The disclosure aims to overcome the shortcomings in the prior art, and develop a device and method for a dry-wet cycle simulation test of concrete in a tidal zone and a splash zone, which can simulate the dry-wet cycle test of concrete structures in a seawater corrosion environment, implement integrated simulation of concrete in the tidal zone and the splash zone, and more truly simulate a marine environment. The device and method can be widely used to simulate the dry-wet cycle test of concrete.

To achieve the above purpose, the disclosure provides the following technical solutions.

In a first aspect, the disclosure provides a device for a dry-wet cycle simulation test of concrete in a tidal zone and a splash zone, including a liquid storage tank and a test chamber, where the liquid storage tank and the test chamber are hollow and communicated with each other, and a communicating pipeline is provided with a valve, tops of both the liquid storage tank and the test chamber are each provided with air holes, an exhaust device and a spraying device are arranged in an upper portion inside the test chamber, and a three-layer support frame for placing concrete samples is arranged below the exhaust device and the spraying device, where the concrete samples placed on the first layer and the second layer are used for simulating a tidal zone environment, and the concrete samples placed on the third layer are used for simulating a splash zone environment, the spraying device is communicated with the inside of the liquid storage tank through a pipeline, water level sensors, a temperature sensor and a temperature and humidity sensor are installed in the test chamber, and the water level sensors, the temperature sensor, the temperature and humidity sensor, the spraying device, the exhaust device and a control valve are connected with a control box.

Further, the water level sensors include a first water level sensor and a second water level sensor, and the first water level sensor and the second water level sensor are mounted on a side wall of the test chamber vertically.

Further, the liquid storage tank is communicated with the test chamber through a pipe support having an n-shaped structure. The pipe support is composed of a first vertical pipe, a second vertical pipe, and a transverse horizontal pipe by connection. The first vertical pipe is located in the liquid storage tank, the second vertical pipe is located in the test chamber, the transverse horizontal pipe is a water inlet pipe, the water inlet pipe is provided with a water inlet pump and a water inlet valve, a water outlet pipe connected with the transverse horizontal pipe is branched from the first vertical pipe, the water outlet pipe is provided with a water outlet pump and a water outlet valve, and spray water pipes are branched from an outlet side of the water inlet valve on the water inlet pipe.

Further, a communicating pipe connected with the liquid storage tank and the test chamber is arranged below the water outlet pipe.

Further, the temperature and humidity sensor is located above a joint of the test chamber and the communicating pipe and configured to monitor the temperature and humidity of the environment where the concrete samples in the splash zone are located, and the temperature sensor is located below a joint of the test chamber and the communicating pipe and configured to monitor the temperature of the environment where the concrete samples in the tidal zone are located.

Further, the control box is internally provided with a single-chip microcomputer circuit board and externally provided with a display screen, and can control operations of the exhaust device, the water level sensors, the temperature and humidity sensor, the temperature sensor, the valve, the water inlet pump, the water inlet valve, the water outlet pump and the water outlet valve, set test parameters and record temperature and humidity.

Further, the liquid storage tank and the test chamber are made of stainless steel resistant to corrosion by salt solution.

In a second aspect, the disclosure provides a test method based on the above test device, specifically including placing concrete samples on each layer of support frame, where the concrete samples on the first layer and the second layer are used for simulating a tidal zone environment, and the concrete samples placed on the third layer are used for simulating a splash zone environment, injecting a salt solution with a set weight into a liquid storage tank, and inputting a dry-wet cycle time ratio and cycle time required by the test into a control box, when the test is started, automatically and preferentially entering a wetting operating state, operating a water inlet pump and a water outlet pump within the time specified by the control box to achieve the purpose of automatic dry-wet cycle, and starting, by the control box, a temperature and humidity sensor and a temperature sensor to record temperatures and humidity when the concrete samples are wet and when the concrete samples are dried, when the concrete samples on the first layer and the second layer are to be soaked and the concrete samples on the third layer are to be showered, switching on a communication valve, the water inlet pump and a water inlet valve by the control box, so that a communicating pipe, a pipe support and spray water pipes are communicated with the liquid storage tank, the salt solution in the liquid storage tank enters a test chamber and then rises to the communicating pipe under the spraying by spray heads, and the salt solution added on this basis flows back to the liquid storage tank through the communicating pipe, when a set wetting time is up, controlling the communication valve, the water inlet pump and the water inlet valve to be switched off by the control box, and switching on the water outlet pump and a water outlet valve by the control box, so that the salt solution flows back to the liquid storage tank, when the concrete samples are in a wet state, shutting down ceiling fans by the control box, after the salt solution flows back to the liquid storage tank, starting the ceiling fans by the control box, discharging water vapor through air holes of the test chamber, and drying the concrete samples, where during the test, the control box can display the dry-wet state, set the dry-wet cycle time ratio according to the test requirements, and record and save records of dry-wet cycle times.

Compared with the prior art, the disclosure has the following advantages:

1. The device is simple in basic structure, convenient to install and high in automation degree, saves a large amount of manpower, material resources and time. A control box can control and record test parameters in real time, and the accuracy is improved.

2. A communicating pipe connecting a liquid storage tank with a test chamber is arranged, so that the boundary between the tidal zone and the splash zone is clear, and during the test process, the tidal zone is always in the soaking environment, while the splash zone is in the spraying environment.

3. The device solves the problem of separate simulation of concrete in the tidal zone and the splash zone, truly simulates the marine environment in an integrated way, and can be widely used to simulate the dry-wet cycle test of concrete.

BRIEF DESCRIPTION OF THE DRAWINGS

The accompany drawings of the specification constituting a part of the disclosure provide further understanding of the disclosure. The schematic examples of the disclosure and description thereof are intended to be illustrative of the disclosure and do not constitute an undue limitation of the disclosure.

DETAILED DESCRIPTION

It should be noted that the following detailed description is exemplary and aims to further describe the disclosure. Unless otherwise specified, all technical and scientific terms used in the disclosure have the same meaning as commonly understood by one of ordinary skill in the technical field to which the disclosure belongs.

It should be noted that the terms used herein are merely used for describing the specific implementations, but are not intended to limit exemplary implementations of the disclosure. As used herein, the singular form is also intended to include the plural form unless otherwise indicated obviously in the disclosure. Furthermore, it should be further understood that the terms "include" and/or "comprise" used in this specification specify the presence of features, steps, operations, devices, components, and/or a combination thereof.

For convenience of description, if the words "up", "down", "left" and "right" appear in the disclosure, they only mean that they are consistent with the up, down, left and right directions of the accompanying drawing itself, and do not limit the structure. They are only for convenience of describing the disclosure and simplifying the description, but do not indicate or imply that referred devices or elements must have a specific orientation and be constructed and operated in a specific orientation, so they cannot be understood as a limitation to the disclosure.

The disclosure will be further described in detail below with reference to the accompanying drawings and examples.

Example 1

Figure 2:
FIG. 2 is a schematic top view of a structure of a support frame according to the disclosure.

A main structure of a device for a dry-wet cycle simulation test of concrete in a tidal zone and a splash zone in this example includes a liquid storage tank 1, a test chamber 2, a communicating pipe 3, air holes 4 of the liquid storage tank, air holes 5 of the test chamber, ceiling fans 6, steel pipes 7, a support frame 8, an upper water level sensor 9, a lower water level sensor 10, a temperature and humidity sensor 11, a temperature sensor 12, a chamber body support 13, a communication valve 14, a pipe support 15, a water inlet pump 16, a water inlet valve 17, a water outlet pipe 18, a water outlet pump 19, a water outlet valve 20, spray water pipes 21, spray heads 22, and a control box 23. FIG. 2 is a schematic top view of a structure of the support frame 8.

The liquid storage tank 1 and the test chamber 2 which are independently arranged and each have the hollow structure are connected through the communicating pipe 3, so that the liquid storage tank 1 and the test chamber 2 can be communicated with each other. The communicating pipe 3 is provided with the communication valve 14.

The top of the liquid storage tank 1 is provided with two rows of parallel air holes 4 of the liquid storage tank. The top of the test chamber 2 is provided with four columns of parallel air holes 5 of the test chamber. The air holes are provided mainly to ensure the stability of the pressure in a chamber body.

The top inside the test chamber 2 is provided with two rows of ceiling fans 6, and the control box 23 controls the wind power, starting and shutdown, etc. of the ceiling fans 6. The ceiling fans 6 mainly function to discharge water vapor inside the test chamber and dry concrete samples.

Two parallel steel pipes 7 are disposed on an upper portion inside the test chamber 2. The steel pipes 7 are mainly used for laying the spray water pipes 21. The support frame 8 with a three-layer structure is arranged at the bottom inside the test chamber 2. The concrete samples are placed on each layer of the support frame 8. The concrete samples placed on the first layer and the second layer are used for simulating a tidal zone environment, and the concrete samples placed on the third layer are used for simulating a splash zone environment.

Figure 1:
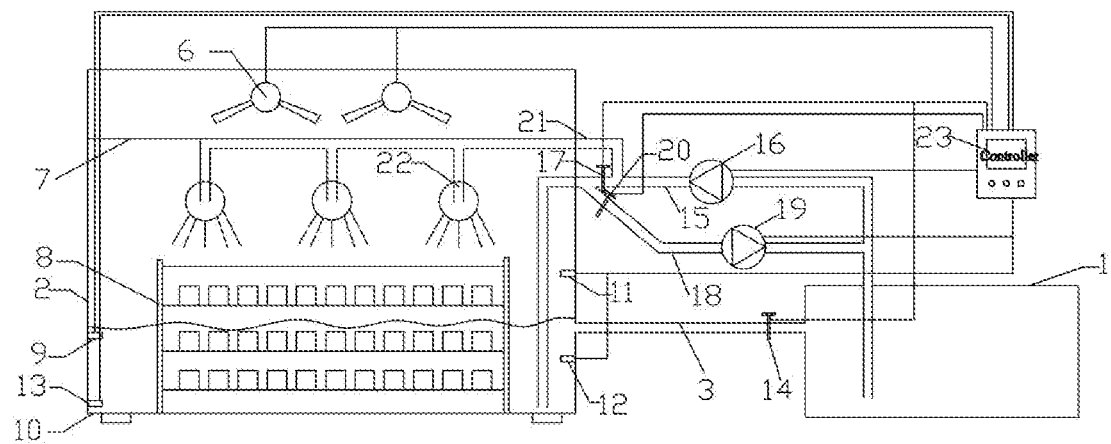
FIG. 1 is a schematic diagram of a main structure of the disclosure.

According to the orientation in FIG. 1, the upper water level sensor 9 and the lower water level sensor 10 are arranged on a left side wall inside the test chamber 2, and the temperature and humidity sensor 11 and the temperature sensor 12 are arranged on a right side wall inside the test chamber 2. The upper water level sensor 9 and the lower water level sensor 10 are used for monitoring the liquid level of the salt solution in the test chamber 2. The temperature and humidity sensor 11 is used for monitoring the temperature and humidity of the test chamber 2.

The chamber body support 13 is arranged at the outer bottom of the test chamber 2 to support the test chamber.

The pipe support 15 is in an n shape and is composed of, by connection, a right vertical pipe arranged on the right side, a left vertical pipe arranged on the left side and a transverse horizontal pipe arranged between the right vertical pipe and the left vertical pipe. The right vertical pipe is arranged in the liquid storage tank, and the left vertical pipe is arranged in the test chamber. The left vertical pipe, the right vertical pipe and the transverse horizontal pipe are communicated with each other. The transverse horizontal pipe is a water inlet pipe, the water inlet pipe is provided with the water inlet pump 16 and the water inlet valve 17. The water outlet pipe 18 connected with the transverse horizontal pipe is branched from the right vertical pipe. The water outlet pipe 18 is provided with the water outlet pump 19 and the water outlet valve 20. Two rows of spray water pipes 21 are branched from a right side of the water inlet valve 17 on the water inlet pipe. The spray water pipes 21 are bound and laid along the steel pipe 7, and a plurality of spray heads 22 are arranged on the spray water pipes 21 at equal intervals. The ceiling fans 6, the upper water level sensor 9, the lower water level sensor 10, the temperature and humidity sensor 11, the temperature sensor 12, the communication valve 14, the water inlet pump 16, the water inlet valve 17, the water outlet pump 19, and the water outlet valve 20 are electrically connected to the control box 23.

The liquid storage tank 1 and the test chamber 2 in this example are made of stainless steel resistant to corrosion by salt solution, and the test chamber 2 has a size of 2 m×1.5 m×2 m. Certainly, it is not difficult to understand that in other examples, the liquid storage tank 1 and the test chamber 2 may also be made of other materials resistant to corrosion by salt solution. The size of the test chamber is set according to actual requirements.

The communicating pipe 3, the upper water level sensor 9, the lower water level sensor 10, the temperature and humidity sensor 11, the temperature sensor 12, the communication valve 14, the water inlet pump 16, the water inlet valve 17, the water outlet pipe 18, the water outlet pump 19, the water outlet valve 20, the spray water pipes 21, and the spray heads 22 are made of materials having corrosion resistance.

Figure 3:
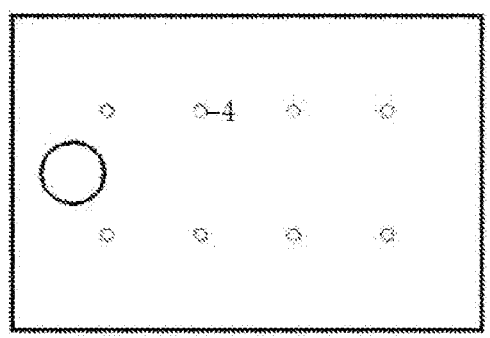
FIG. 3 is a schematic diagram showing the distribution of air holes of a liquid storage tank according to the disclosure.

As shown in FIG. 3, there are 8 air holes 4 of the liquid storage tank which are divided into two rows and four columns and used to keep the internal air pressure of the liquid storage tank 1 stable. Certainly, it is not difficult to understand that in other examples, the number of the air holes 4 of the liquid storage tank is not limited to 8, and the specific number is set according to the size of the liquid storage tank 1.

Figure 4:
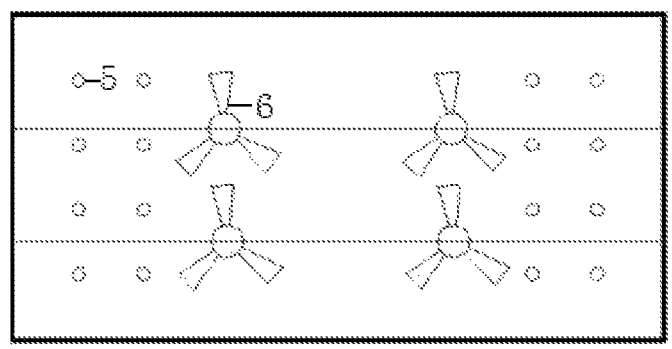
FIG. 4 is a schematic diagram showing the distribution of air holes of a test chamber and ceiling fans according to the disclosure.

As shown in FIG. 4, there are 16 air holes 5 of the test chamber which are divided into four rows and eight columns and used to discharge water vapor out of the test chamber 2. Certainly, it is not difficult to understand that in other examples, the number and arrangement modes of air holes 5 of the test chamber are set according to the size and shape of the test chamber.

Figure 5:
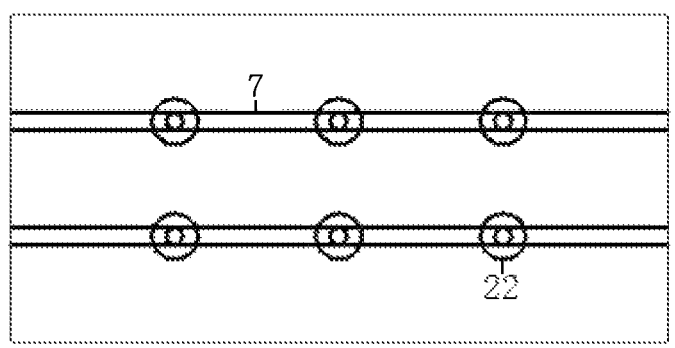
FIG. 5 is a schematic diagram showing the distribution of steel pipe and spray heads according to the disclosure.

FIG. 5 is a schematic diagram showing the distribution of steel pipe 7 and spray heads 22. The steel pipes 7 in this example are used to fix the spray water pipes 21 and the spray heads 22. The spray heads 22 are arranged on the spray water pipes 21. The number of the spray heads 22 is set according to actual needs.

The support frame 8 in this example is a corrosion-resistant stainless steel frame with a size of 1.8 m×1.3 m×1 m formed by welding steel pipes at intervals.

The temperature and humidity sensor 11 in this example is located above a joint of the test chamber 2 and the communicating pipe 3 and configured to monitor the temperature and humidity of the environment where the concrete samples in the splash zone are located, and the temperature sensor 12 is located below a joint of the test chamber 2 and the communicating pipe 3 and configured to monitor the temperature of the environment where the concrete samples in the tidal zone are located.

The control box 23 in this example is internally provided with a single-chip microcomputer circuit board and externally provided with a display screen, and can control operations of the ceiling fans 6, the upper water level sensor 9, the lower water level sensor 10, the temperature and humidity sensor 11, the temperature sensor 12, the communication valve 14, the water inlet pump 16, the water inlet valve 17, the water outlet pump 19, and the water outlet valve 20, set test parameters and record temperature and humidity.

The test method based on the test device is further described below with reference to specific examples.

The wind force in Qingdao is more affected by the ocean than inland. The prevailing wind directions in summer are south and southeast and the wind power is at 3-4 grades, the dominant wind direction in winter is northwest and the wind power is at 3-5 grades, and the wind directions in spring and autumn are south and southwest and the wind power is at 3-4 grades. When the device for a dry-wet cycle simulation test of concrete in a tidal zone and a splash zone in this example is used to simulate Qingdao sea area for testing, the maximum wind speed of the ceiling fans 6 is set to 10 m/s through the control box 23. The dry-wet cycle time ratio of 3:1 and the cycle time of 1 day required by the test are input into the control box 23.

Concrete samples are placed on each layer of the support frame. The concrete samples placed on the first layer and the second layer are used for simulating a tidal zone environment, and the concrete samples placed on the third layer are used for simulating a splash zone environment.

When the test starts, the device may automatically enter the wetting operating state. The control box 23 switches on the communication valve 14, the water inlet pump 16 and the water inlet valve 17 and shuts down the ceiling fans 6, and the salt solution in the liquid storage tank 1 enters the test chamber 2. When the salt solution level reaches the position of the upper water level sensor 9, the control box 23 switches off the water inlet valve 17.

When the test time is increased to 6 hours, the device enters the drying operating state, the control box 23 shuts down the communication valve 14, water outlet pump 16 and the water outlet valve 17, and starts the ceiling fans 6, the water outlet pump 19, and the water outlet valve 20. The salt solution enters the liquid storage tank 1 from the test chamber 2. When the water level in the test chamber 2 drops to the position of the lower water level sensor 12, the control box switches off the water outlet pump 19 and the water outlet valve 20, and when the test time is increased to 24 hours, the device enters the wetting operating state again.

The water inlet pump and the water outlet pump operate within the time specified by the control box to achieve the purpose of automatic dry-wet cycle, and the control box starts the temperature and humidity sensor and the temperature sensor to record temperatures and humidity when the concrete samples are wet and when the concrete samples are dried. Specifically, when the concrete samples on the first layer and the second layer are to be soaked and the concrete samples on the third layer are to be showered, the control box switches on the communication valve, the water inlet pump and the water inlet valve, so that the communicating pipe, the pipe support and the spray water pipes are communicated with the liquid storage tank, the salt solution in the liquid storage tank enters the test chamber and then rises to the communicating pipe under the spraying by the spray heads, and the salt solution added on this basis flows back to the liquid storage tank through the communicating pipe, when a set wetting time is up, the control box controls the communication valve, the water inlet pump and the water inlet valve to be switched off, and the control box switches on the water outlet pump and a water outlet valve, so that the salt solution flows back to the liquid storage tank, when the concrete samples are in a wet state, the control box shuts down ceiling fans, after the salt solution flows back to the liquid storage tank, the control box starts the ceiling fans, water vapor is discharged through the air holes of the test chamber, and the concrete samples are dried, and during the test, the control box can display the dry-wet state, set the dry-wet cycle time ratio according to the test requirements, and record and save records of dry-wet cycle times.

The foregoing is merely illustrative of the examples of the disclosure and is not intended to limit the disclosure, and various changes and modifications may be made by those skilled in the art. Any modifications, equivalent replacements, improvements, and the like within the spirit and principles of the disclosure should fall within the protection scope of the disclosure.

What is claimed is:

1. A device for a dry-wet cycle simulation test of concrete in a tidal zone and a splash zone, the device comprising a liquid storage tank and a test chamber;
    wherein the liquid storage tank and the test chamber are hollow and in communication with each other, wherein a communicating pipeline is provided with a valve, and wherein tops of both the liquid storage tank and the test chamber are each provided with air holes; and
    wherein an exhaust device and a spraying device are arranged in an upper portion inside the test chamber, wherein a three-layer support frame for placing concrete samples is arranged below the exhaust device and the spraying device, wherein the concrete samples placed on the first layer and the second layer are used for simulating a tidal zone environment, wherein the concrete samples placed on the third layer are used for simulating a splash zone environment, wherein the spraying device is in communication with the inside of the liquid storage tank through a pipeline, wherein water level sensors, a temperature sensor, and a temperature and humidity sensor are installed in the test chamber, and wherein the water level sensors, the temperature sensor, the temperature and humidity sensor, the spraying device, the exhaust device, and a control valve are connected with a control box;
    wherein the liquid storage tank is in communication with the test chamber through a pipe support having an n-shaped structure, wherein the pipe support comprises a first vertical pipe, a second vertical pipe, and a transverse horizontal pipe by connection, wherein the first vertical pipe is located in the liquid storage tank, wherein the second vertical pipe is located in the test chamber, wherein the transverse horizontal pipe is a water inlet pipe, wherein the water inlet pipe is provided with a water inlet pump and a water inlet valve, wherein a water outlet pipe connected with the transverse horizontal pipe branches from the first vertical pipe, wherein the water outlet pipe is provided with a water outlet pump and a water outlet valve, and wherein spray water pipes branch from an outlet side of the water inlet valve on the water inlet pipe.

2. The device for a dry-wet cycle simulation test of concrete in a tidal zone and a splash zone according to claim 1, wherein the water level sensors comprise a first water level sensor and a second water level sensor, and wherein the first water level sensor and the second water level sensor are mounted on a side wall of the test chamber vertically.

3. The device for a dry-wet cycle simulation test of concrete in a tidal zone and a splash zone according to claim 1, wherein the liquid storage tank and the test chamber are made of stainless steel resistant to corrosion by salt solution.

4. The device for a dry-wet cycle simulation test of concrete in a tidal zone and a splash zone according to claim 1, wherein a communicating pipe connected with the liquid storage tank and the test chamber is arranged below the water outlet pipe.

5. The device for a dry-wet cycle simulation test of concrete in a tidal zone and a splash zone according to claim 4, wherein the temperature and humidity sensor is located above a joint of the test chamber and the communicating pipe and is configured to monitor a temperature and humidity of the splash zone environment where the concrete samples in the splash zone are located, and wherein the temperature sensor is located below a joint of the test chamber and the communicating pipe and configured to monitor a temperature of the tidal zone environment where the concrete samples in the tidal zone are located.

6. The device for a dry-wet cycle simulation test of concrete in a tidal zone and a splash zone according to claim 5, wherein the control box is internally provided with a single-chip microcomputer circuit board and externally provided with a display screen, wherein the control box is capable of controlling operations of the exhaust device, the water level sensors, the temperature and humidity sensor, the temperature sensor, the control valve, the water inlet pump, the water inlet valve, the water outlet pump, and the water outlet valve, and wherein the control box can set is capable of setting test parameters and a record temperature and humidity.

7. A test method based on the test device according to claim 1, specifically the test method comprising:
    placing the concrete samples on each layer of support frame, wherein the concrete samples on the first layer and the second layer are used for simulating the tidal zone environment, and wherein the concrete samples placed on the third layer are used for simulating the splash zone environment, injecting a salt solution with a set weight into the liquid storage tank, and inputting a dry-wet cycle time ratio and cycle time required by the test into the control box;

when the test is started, automatically entering a wetting operating state, operating the water inlet pump and the water outlet pump within the time specified by the control box to achieve the purpose of automatic dry-wet cycle, and starting, by the control box, the temperature and humidity sensor and the temperature sensor to record temperatures and humidity when the concrete samples are wet and when the concrete samples are dried;

when the concrete samples on the first layer and the second layer are to be soaked and the concrete samples on the third layer are to be showered, switching on a communication valve, the water inlet pump, and the water inlet valve by the control box, so that a communicating pipe, the pipe support, and the spray water pipes are in communication with the liquid storage tank, the salt solution in the liquid storage tank enters the test chamber and then rises to the communicating pipe under the spraying by spray heads, and the salt solution added on this basis flows back to the liquid storage tank through the communicating pipe;

when a set wetting time is up, controlling the communication valve, the water inlet pump, and the water inlet valve to be switched off by the control box, and switching on the water outlet pump and the water outlet valve by the control box, so that the salt solution flows back to the liquid storage tank;

when the concrete samples are in a wet state, shutting down ceiling fans by the control box;

after the salt solution flows back to the liquid storage tank, starting the ceiling fans by the control box, discharging water vapor through the air holes of the test chamber, and drying the concrete samples, wherein during the test, the control box is capable of displaying the dry-wet state, set the dry-wet cycle time ratio according to the test requirements, and record and save records of dry-wet cycle times.

8. A test method based on the test device according to claim 2, the test method comprising:

placing the concrete samples on each layer of support frame, wherein the concrete samples on the first layer and the second layer are used for simulating the tidal zone environment, and wherein the concrete samples placed on the third layer are used for simulating the splash zone environment, injecting a salt solution with a set weight into the liquid storage tank, and inputting a dry-wet cycle time ratio and cycle time required by the test into the control box;

when the test is started, automatically entering a wetting operating state, operating the water inlet pump and the water outlet pump within the time specified by the control box to achieve the purpose of automatic dry-wet cycle, and starting, by the control box, the temperature and humidity sensor and the temperature sensor to record temperatures and humidity when the concrete samples are wet and when the concrete samples are dried;

when the concrete samples on the first layer and the second layer are to be soaked and the concrete samples on the third layer are to be showered, switching on a communication valve, the water inlet pump, and the water inlet valve by the control box, so that a communicating pipe, the pipe support, and the spray water pipes are in communication with the liquid storage tank, the salt solution in the liquid storage tank enters the test chamber and then rises to the communicating pipe under the spraying by spray heads, and the salt solution added on this basis flows back to the liquid storage tank through the communicating pipe;

when a set wetting time is up, controlling the communication valve, the water inlet pump, and the water inlet valve to be switched off by the control box, and switching on the water outlet pump and the water outlet valve by the control box, so that the salt solution flows back to the liquid storage tank;

when the concrete samples are in a wet state, shutting down ceiling fans by the control box;

after the salt solution flows back to the liquid storage tank, starting the ceiling fans by the control box, discharging water vapor through the air holes of the test chamber, and drying the concrete samples, wherein during the test, the control box is capable of displaying the dry-wet state, set the dry-wet cycle time ratio according to the test requirements, and record and save records of dry-wet cycle times.

9. A test method based on the test device according to claim 4, the test method comprising:

placing the concrete samples on each layer of support frame, wherein the concrete samples on the first layer and the second layer are used for simulating the tidal zone environment, and wherein the concrete samples placed on the third layer are used for simulating the splash zone environment, injecting a salt solution with a set weight into the liquid storage tank, and inputting a dry-wet cycle time ratio and cycle time required by the test into the control box;

when the test is started, automatically entering a wetting operating state, operating the water inlet pump and the water outlet pump within the time specified by the control box to achieve the purpose of automatic dry-wet cycle, and starting, by the control box, the temperature and humidity sensor and the temperature sensor to record temperatures and humidity when the concrete samples are wet and when the concrete samples are dried;

when the concrete samples on the first layer and the second layer are to be soaked and the concrete samples on the third layer are to be showered, switching on a communication valve, the water inlet pump, and the water inlet valve by the control box, so that the communicating pipe, the pipe support, and the spray water pipes are in communication with the liquid storage tank, the salt solution in the liquid storage tank enters the test chamber and then rises to the communicating pipe under the spraying by spray heads, and the salt solution added on this basis flows back to the liquid storage tank through the communicating pipe;

when a set wetting time is up, controlling the communication valve, the water inlet pump, and the water inlet valve to be switched off by the control box, and switching on the water outlet pump and the water outlet valve by the control box, so that the salt solution flows back to the liquid storage tank;

when the concrete samples are in a wet state, shutting down ceiling fans by the control box;

after the salt solution flows back to the liquid storage tank, starting the ceiling fans by the control box, discharging water vapor through the air holes of the test chamber, and drying the concrete samples, wherein during the test, the control box is capable of displaying the dry-wet state, set the dry-wet cycle time ratio according to the test requirements, and record and save records of dry-wet cycle times.

10. A test method based on the test device according to claim 5, the test method comprising:

placing the concrete samples on each layer of support frame, wherein the concrete samples on the first layer and the second layer are used for simulating the tidal zone environment, and wherein the concrete samples placed on the third layer are used for simulating the splash zone environment, injecting a salt solution with a set weight into the liquid storage tank, and inputting a dry-wet cycle time ratio and cycle time required by the test into the control box;

when the test is started, automatically entering a wetting operating state, operating the water inlet pump and the water outlet pump within the time specified by the control box to achieve the purpose of automatic dry-wet cycle, and starting, by the control box, the temperature and humidity sensor and the temperature sensor to record temperatures and humidity when the concrete samples are wet and when the concrete samples are dried;

when the concrete samples on the first layer and the second layer are to be soaked and the concrete samples on the third layer are to be showered, switching on a communication valve, the water inlet pump, and the water inlet valve by the control box, so that the communicating pipe, the pipe support, and the spray water pipes are in communication with the liquid storage tank, the salt solution in the liquid storage tank enters the test chamber and then rises to the communicating pipe under the spraying by spray heads, and the salt solution added on this basis flows back to the liquid storage tank through the communicating pipe;

when a set wetting time is up, controlling the communication valve, the water inlet pump, and the water inlet valve to be switched off by the control box, and switching on the water outlet pump and the water outlet valve by the control box, so that the salt solution flows back to the liquid storage tank;

when the concrete samples are in a wet state, shutting down ceiling fans by the control box;

after the salt solution flows back to the liquid storage tank, starting the ceiling fans by the control box, discharging water vapor through the air holes of the test chamber, and drying the concrete samples, wherein during the test, the control box is capable of displaying the dry-wet state, set the dry-wet cycle time ratio according to the test requirements, and record and save records of dry-wet cycle times.

11. A test method based on the test device according to claim 6, the test method comprising:

placing the concrete samples on each layer of support frame, wherein the concrete samples on the first layer and the second layer are used for simulating the tidal zone environment, and wherein the concrete samples placed on the third layer are used for simulating the splash zone environment, injecting a salt solution with a set weight into the liquid storage tank, and inputting a dry-wet cycle time ratio and cycle time required by the test into the control box;

when the test is started, automatically entering a wetting operating state, operating the water inlet pump and the water outlet pump within the time specified by the control box to achieve the purpose of automatic dry-wet cycle, and starting, by the control box, the temperature and humidity sensor and the temperature sensor to record temperatures and humidity when the concrete samples are wet and when the concrete samples are dried;

when the concrete samples on the first layer and the second layer are to be soaked and the concrete samples on the third layer are to be showered, switching on a communication valve, the water inlet pump, and the water inlet valve by the control box, so that the communicating pipe, the pipe support, and the spray water pipes are in communication with the liquid storage tank, the salt solution in the liquid storage tank enters the test chamber and then rises to the communicating pipe under the spraying by spray heads, and the salt solution added on this basis flows back to the liquid storage tank through the communicating pipe;

when a set wetting time is up, controlling the communication valve, the water inlet pump, and the water inlet valve to be switched off by the control box, and switching on the water outlet pump and the water outlet valve by the control box, so that the salt solution flows back to the liquid storage tank;

when the concrete samples are in a wet state, shutting down ceiling fans by the control box;

after the salt solution flows back to the liquid storage tank, starting the ceiling fans by the control box, discharging water vapor through the air holes of the test chamber, and drying the concrete samples, wherein during the test, the control box is capable of displaying the dry-wet state, set the dry-wet cycle time ratio according to the test requirements, and record and save records of dry-wet cycle times.

12. A test method based on the test device according to claim 3, the test method comprising:

placing the concrete samples on each layer of support frame, wherein the concrete samples on the first layer and the second layer are used for simulating the tidal zone environment, and wherein the concrete samples placed on the third layer are used for simulating the splash zone environment, injecting the salt solution with a set weight into the liquid storage tank, and inputting a dry-wet cycle time ratio and cycle time required by the test into the control box;

when the test is started, automatically entering a wetting operating state, operating the water inlet pump and the water outlet pump within the time specified by the control box to achieve the purpose of automatic dry-wet cycle, and starting, by the control box, the temperature and humidity sensor and the temperature sensor to record temperatures and humidity when the concrete samples are wet and when the concrete samples are dried;

when the concrete samples on the first layer and the second layer are to be soaked and the concrete samples on the third layer are to be showered, switching on a communication valve, the water inlet pump, and the water inlet valve by the control box, so that a communicating pipe, the pipe support, and the spray water pipes are in communication with the liquid storage tank, the salt solution in the liquid storage tank enters the test chamber and then rises to the communicating pipe under the spraying by spray heads, and the salt solution added on this basis flows back to the liquid storage tank through the communicating pipe;

when a set wetting time is up, controlling the communication valve, the water inlet pump, and the water inlet valve to be switched off by the control box, and switching on the water outlet pump and the water outlet valve by the control box, so that the salt solution flows back to the liquid storage tank;

when the concrete samples are in a wet state, shutting down ceiling fans by the control box;

after the salt solution flows back to the liquid storage tank, starting the ceiling fans by the control box, discharging water vapor through the air holes of the test chamber, and drying the concrete samples, wherein during the test, the control box is capable of displaying the dry-wet state, set the dry-wet cycle time ratio according to the test requirements, and record and save records of dry-wet cycle times.

\* \* \* \* \*